United States Patent [19]

Gremm et al.

[11] Patent Number: 4,925,672
[45] Date of Patent: May 15, 1990

[54] PRODUCTS CONTAINING A CALCIUM ANTAGONIST AND A LIPID-LOWERING AGENT

[75] Inventors: Dorothee Gremm, Mannheim; Ingetraud Perstel, Mannheim-Feudenheim, both of Fed. Rep. of Germany

[73] Assignee: Knoll AG, Ludwigshafen, Fed. Rep. of Germany

[21] Appl. No.: 318,825

[22] Filed: Mar. 6, 1989

[30] Foreign Application Priority Data

Mar. 10, 1988 [DE] Fed. Rep. of Germany ....... 3807895

[51] Int. Cl.$^5$ ................................................ A61K 9/48
[52] U.S. Cl. ....................................... 424/451; 424/456; 424/457; 424/459; 424/469; 424/470; 424/489; 424/499; 424/501; 514/523
[58] Field of Search ............... 424/470, 469, 451, 489, 424/457, 459, 456, 499, 501; 514/523

[56] References Cited

U.S. PATENT DOCUMENTS

| | | | |
|---|---|---|---|
| 4,558,058 | 12/1985 | Schönafinger | 546/257 |
| 4,695,465 | 9/1987 | Kigasawa | 424/449 |
| 4,801,460 | 1/1989 | Goertz | 424/468 |

OTHER PUBLICATIONS

Bungeroth, Fortschr. Med. (DE), 1987, 105/31 (607–611).
Furberg et al, Am. J. Med. (U.S.A.), 1984, 76/6A (76–83).
Scrip World Pharmaceutical News, 1988, No. 1320, pp. 28–29.
Scrip World Pharmaceutical News No. 884, pp. 6–8.
Scrip World Pharmaceutical News No. 842, p. 2.
Burberg, Am. J. Med., 76 (6A); 76–83, Jun. 22, 1984.
Leisz et al., Aktuel. Neurol. (DE), 1984, 11/4 (129–133).
Pedersen, Ugeskr. Laeg. (Denmark), 1982, 144/29 (2156–2164).
Therapiewoche, vol. 38, pp. 136–139, 1988 (English summary only).
Klin Worchenschr, vol. 66, Suppl. XIII, 1988.

*Primary Examiner*—Thurman K. Page
*Assistant Examiner*—Amy Hulina
*Attorney, Agent, or Firm*—Oblon, Spivak, McClelland, Maier & Neustadt

[57] ABSTRACT

Combinations of calcium antagonists and lipid-lowering agents are suitable for controlling diseases.

7 Claims, No Drawings

PRODUCTS CONTAINING A CALCIUM ANTAGONIST AND A LIPID-LOWERING AGENT

It is known that calcium antagonists are effective drugs for the treatment of coronary heart disease (H. Eichstädt, Calcium-Antagonisten, Chapter 33 in Handbuch der inneren Medizin, Volume IX/3: Koronarerkrankungen, Editor H. Roskamm, Springer-Verlag, Berlin, 1984; U. Borchard, Spektrum Koronartherapeutika, Aesopus Verlag, Zug, 1985).

Furthermore, a number of lipid-lowering agents which can be used for the treatment of hyperlipidemia have been described (W. Kruse et al., Spektrum Lipidsenker, Aesopus Verlag, Zug, 1985). It is also known that fibrates improve the flow properties of the blood (eg. Ernst/Matrai, Therapiewoche 38 (1988), 136–139; Lecture by Leschke at the experts' discussion Aktueller Stand der Therapie von Fettstoffwechselstörungen, Wiesbaden, Oct. 10 1987; Ärzte-Zeitung 6 (1987), 29).

We have found that the action of calcium antagonists can be improved by adding lipid-lowering agents.

The present invention relates to products containing a calcium antagonist and a lipid-lowering agent.

The products may be in the form of combination preparations for simultaneous use in a fixed combination or as separate components for use simultaneously or sequentially.

Particular examples of calcium antagonists are diltiazem, etafenone, fendiline, gallopamil, nifedipine, prenylamine, perhexiline and verapamil. Among these, verapamil and gallopamil are preferred.

Examples of suitable lipid-lowering agents are bezafibrate, clofibrate and aluminum clofibrate and etofylline clofibrate, colestipol, colestyramine, dextrothyroxine, etiroxate, etofibrate, fenofibrate, gemfibrozil, inositol nicotinate, magnesium pyridoxal 5'-phosphate glutamate, probucol, 3-pyridylmethanol, β-sitosterol and xantinol nicotinate. Among these substances, the fibrates (benzafibrate, clofibrate, etofibrate and fenofibrate) are preferred.

If the substances contain basic groups, they can also be used for the combination preparation in the form of their salts with physiologically tolerated acids. Suitable and preferred physiologically tolerated acids are hydrochloric acid, sulfuric acid, phosphoric acid, acetic acid, citric acid, malonic acid, salicylic acid, maleic acid, fumaric acid, succinic acid, ascorbic acid, malic acid, methanesulfonic acid, lactic acid, gluconic acid, glucuronic acid, amidosulfonic acid, benzoic acid and tartaric acid.

The calcium antagonist and lipid-lowering agent are present in the mixture in amounts which are at the lower limit of the doses usually recommended for these substances, or somewhat below this limit. As a rule, the ratio of the amounts of lipid-lowering agent to calcium antagonist is from 10:1 to 1:10. For a combination of verapamil and fenofibrate, this ratio is preferably from 1:2 to 2:1.

The novel combination improves the flow properties of the blood in an unexpected synergistic manner compared with the individual components of the combination. It is therefore suitable for the therapy and prevention of symptoms due to disturbances of myocardial blood flow in coronary heat disease, ie. all angina pectoris forms, for the aftertreatment of myocardial infarction and for use before and after balloon angioplasty and bypass operations.

The novel products can be administered parenterally but are preferably administered orally. Tablets, coated tablets and capsules are particularly suitable for oral administration. Sustained-release forms are especially suitable. The known processes, as described in, for example, H. Sucker et al., Pharmazeutische Technologie, Thieme-Verlag, Stuttgart 1978, are suitable for the preparation of the stated forms. It is also possible possible to convert the individual components of the mixture into administration forms and to pack these together, for example in a blister pack.

EXAMPLE 1

20 Isoptin ®RR sustained-release tablets and 20 Normalip ® sustained-release capsules were introduced in pairs into each blister pack.

EXAMPLE 2

Pellets having the following composition were prepared:

| (a) | fenofibrate | 100.00 mg |
|---|---|---|
|  | sucrose | 17.92 mg |
|  | corn starch | 5.96 mg |
|  | polyvidone | 0.74 mg |
|  | talc | 1.49 mg |
|  | polymethacrylic acid L* | 1.44 mg |
|  | polymethacrylic acid E* | 0.40 mg |
|  | stearic acid | 0.05 mg |
|  |  | 128.00 mg |
| (b) | verapamil hydrochloride | 100.00 mg |
|  | colloidal silica | 1.00 mg |
|  | corn starch | 6.96 mg |
|  | sugar pellets | 22.65 mg |
|  | ethylcellulose | 3.40 mg |
|  | glycerol mono-/dioleate | 2.27 mg |
|  | ® Eudragit RS** | 1.45 mg |
|  | ® Eudragit S*** | 2.90 mg |
|  | dibutyl phthalate | 0.29 mg |
|  | talc | 9.38 mg |
|  |  | 150.30 mg |

*Manufacturer: Rohm, Darmstadt
**Polymer of acrylates and methacrylates having a low content of quaternary ammonium groups (manufacturer: Rohm, Darmstadt)
***Anionic polymer of methacrylic acid and methacrylates (manufacturer: Rohm, Darmstadt) 128.0 mg of pellets (a) and 150.3 mg of pellets (b) were introduced into each hard gelatine capsules.

EXAMPLE 3

Example 2 was repeated, except that 192.0 mg of pellets (a) and 150.3 mg of pellets (b) were introduced per hard gelatine capsule.

EXAMPLE 4

Example 2 was repeated, except that 128.0 mg of pellets (a) and 300.6 mg of pellets (b) were introduced per hard gelatine capsule.

EXAMPLE 5

Tablets having the following composition were compressed:

| (a) | fenofibrate | 80.00 |
|---|---|---|
|  | sucrose | 14.35 |
|  | corn starch | 4.77 |
|  | polyvidone | 0.59 |
|  | talc | 1.19 |
| (b) | verapamil hydrochloride | 80.00 |
|  | colloidal silica | 0.80 |
|  | corn starch | 5.60 |
|  | sugar pellets | 18.17 |
|  | ethylcellulose | 2.72 |

| -continued | |
|---|---|
| glycerol mono-/dioleate | 1.81 |
| talc | 7.50 |

The tablets were introduced into capsules in the ratio of 1:1.

We claim:

1. A product containing the calcium antagonist verapamil and the lipid-lowering agent fenofibrate in the ratio of 10:1 to 1:10.

2. A product as claimed in claim 1, as a combination preparation for simultaneous use in a fixed combination.

3. A product as claimed in claim 1, wherein the ratio of verapamil to fenofibrate is from 1:2 to 2:1.

4. A product as claimed in claim 1, for use to treat diseases.

5. The method for treatment of disturbances of myocardial blood flow in coronary heart disease in a subject requiring such treatment which comprises administering to said subject simultaneously an effective amount of verapamil and of fenofibrate in the ratio of 10:1 to 1:10 in the form of a tablet, coated tablet or capsules.

6. The method of claim 5, wherein the ratio of the amount of administered verapamil to that of fenofibrate is 1:2 to 2:1.

7. A pharmaceutical product useful for treatment of disturbances of myocardial blood flow in coronary heart disease comprising a package containing a unit dosage as a tablet, coated tablet or capsule of verapamil copackaged in the package with a unit dosage as a tablet, coated tablet or capsule of fenofibrate, the ratio of the amount of verapamil to that of fenofibrate in the package being 10:1 to 1:10.

* * * * *

UNITED STATES PATENT AND TRADEMARK OFFICE
CERTIFICATE OF CORRECTION

PATENT NO.  : 4,925,672

DATED       : MAY 15, 1990

INVENTOR(S) : DOROTHEE GREMM ET AL.

It is certified that error appears in the above-identified patent and that said Letters Patent is hereby corrected as shown below:

Title page:

In the inventors, delete "Perstel" and insert --Persiel--.

Signed and Sealed this

Eleventh Day of June, 1991

Attest:

HARRY F. MANBECK, JR.

Attesting Officer

Commissioner of Patents and Trademarks